(12) United States Patent
Wang et al.

(10) Patent No.: US 6,448,085 B1
(45) Date of Patent: Sep. 10, 2002

(54) QUALITY CONTROL MATERIAL AND CALIBRATOR FOR NUCLEATED RED BLOOD CELL TESTED ON HEMATOLOGY ANALYZER

(75) Inventors: Fu-sheng Wang, Thousand Oaks; Robin Hagbloom, Claremont, both of CA (US)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 09/833,767

(22) Filed: Apr. 13, 2001

(51) Int. Cl.⁷ .............................................. G01N 31/00
(52) U.S. Cl. .............................. 436/10; 436/8; 436/63; 436/164; 436/166; 436/172; 435/2; 435/29; 435/39
(58) Field of Search ................................ 436/8, 10, 16, 436/18, 63, 164, 166, 172; 435/2, 29, 39; 252/408.1

(56) References Cited

U.S. PATENT DOCUMENTS

| | | | | |
|---|---|---|---|---|
| 5,559,037 A | * | 9/1996 | Kim et al. | 356/317 |
| 5,648,225 A | * | 7/1997 | Kim et al. | 424/154.1 |
| 5,858,790 A | * | 1/1999 | Kim et al. | 436/10 |
| 5,874,310 A | * | 2/1999 | Li et al. | 436/10 |
| 5,879,900 A | * | 3/1999 | Kim et al. | 356/39 |
| 5,917,584 A | * | 6/1999 | Li et al. | 356/39 |
| 6,200,500 B1 | * | 3/2001 | Ryan | 252/408.1 |
| 6,221,668 B1 | * | 4/2001 | Ryan et al. | 252/408.1 |

OTHER PUBLICATIONS

Ruzicka et al. The New Hematology Analyzer Sysmex XE–2100–Performance Evaluation of a Novel White Blood Cell Differential Technology. Archives of Pathology and Laboratory Medicine. vol. 125 (3), Mar. 2001, pp. 391–396.*

* cited by examiner

*Primary Examiner*—Maureen M. Wallenhorst
(74) *Attorney, Agent, or Firm*—Shinjyu Global IP Counselors, LLP

(57) ABSTRACT

A method for the quality control of nucleated red blood cells on a hematology analyzer using a mixture of human and animal blood, particularly chicken blood and fixed human blood with nucleated red blood cells. The control material illustrated good stability over a fifty day period when stored at 4 degrees Celsius. The cell morphology showed good cell shape and the equipment had a stable nucleated red blood cell number and nucleated red blood cell per 100 white blood cells number. The method is used for quality control as for calibration for nucleated red blood cell counting or staging, on a hematology analyzer.

7 Claims, 8 Drawing Sheets

QUALITY CONTROL MATERIAL AND CALIBRATOR FOR NUCLEATED RED BLOOD CELL TESTED ON HEMATOLOGY ANALYZER

BACKGROUND OF THE INVENTION

1. Field of the Invention

The present invention generally relates to methods for counting and staging of nucleated red blood cells (NRBC). More specifically, the present invention relates to the quality control and calibration of nucleated red blood cell counting and staging on automatic hematology analyzers, which allows the hematology analyzers to use the methods to ensure a mode of accurate and precise counting and staging. The invention is directed to using a new control material for nucleated red blood cell counting and staging.

2. Background Information

In a clinical laboratory, particularly when a cell analyzer is used, a calibrator and quality control material is necessary to enable the instrument to perform at a continuously optimal level to ensure accurate and precise results that can be reported.

For example, when using a hematology analyzer, fresh blood is used as a control material. Fixed blood and various types of latex beads are used to provide longer control times to observe any change in a given time frame and observe data results for any necessary calibration change.

Another calibration example can be viewed on a flow cytometer. To guarantee proper working conditions of the instrument, fluorescent labeled beads and animal blood have been used as control materials.

In normal situations of erythropoiesis, there are no nucleated red blood cells found in human peripheral blood except for a short time in neonate blood. When nucleated red blood cells found appear in peripheral blood, it is always an indication of a pathologic situation. Peripheral nucleated red blood cell counting is clinically useful in that it corrects for white blood cell counts and also gives clinicians a basis for diagnosis and prognosis of diseases using peripheral nucleated red blood cell blood. When nucleated red blood cells appear in the peripheral blood, they are counted as white blood cells with a traditional hematology analyzer. This count occurs due to the similar physical characteristics of the two types of cells. When nucleated red blood cells can be separated from white blood cells by a hematology analyzer, it can provide more accurate white blood cell numbers and important information for the diagnosis and prognosis of the diseases with peripheral blood nucleated red blood cells. Therefore, measurement of nucleated red blood cells is very important for clinicians to be able to decipher diseases more easily. This measurement can allow for a quicker diagnosis.

Traditionally, nucleated red blood cells have been counted using a manual method. However, these methods were laborious and time consuming. To obtain a more sensitive, faster, and a less expensive method, nucleated red blood cell measurement using automatic hematology analyzers, has been developed. To make sure the detection method can work correctly, a quality control material is necessary. The control material has to include cell populations of white blood cells and nucleated red blood cells, so that a nucleated red blood cell number, and a nucleated red blood cell count per 100 white blood cells, are available. The control material must also remain stable in order to monitor and to necessitate any change in calibration on a hematology analyzer.

In view of the above, there exists a need for the quality control and calibration of nucleated red blood cell counting and staging on automatic hematology analyzers. This methodology allows the hematology analyzers to use a desired method to ensure a mode of accurate and precise counting and staging which overcomes the above-mentioned problems in the existing art.

It is an objective of this invention to provide a new control material that can be used for nucleated red blood cell counting and staging.

SUMMARY OF THE INVENTION

The present invention provides methods for the quality control and calibration of nucleated red blood cell counting and staging. The methodology uses a new control material made from a mixture of human blood and chicken red blood cells, or fixed human blood alone.

(1) First, a preferred embodiment of the invention uses fixed chicken red blood cells with nuclei that can be used to provide fluorescent signals as seen in real human nucleated red blood cells.

(a) A fixed human peripheral blood sample from an SF-check, a control material for Sysmex hematology analyzers is used and mixed with chicken red blood cells, for example, from BioSure; and (b) The mixed blood was tested on the hematology analyzer in different ways.

(2) Second, the mixture of fixed human blood and chicken blood is analyzed on an automated hematology analyzer, such as the XE-2100.

(3) Third, the diluted chicken red blood cells are measured using different concentrations in SF-check to analyze the linearity of nucleated red blood cells represented by chicken red blood cells.

(4) Fourth, nucleated red blood cell concentration is measured in different mixtures that included mixture with SF-check in high, normal and low concentrations, having the ratios of 1:1 to 1:9 to obtain the different nucleated red blood cell counting levels.

(5) Fifth, the mixture of blood is kept at 4° C. in order to check the stability of the mixture and count the nucleated red blood cell number and nucleated red blood cell count per 100 white blood cells.

An alternate embodiment of the invention uses fixed human blood.

(1) The human blood, namely human peripheral blood, or umbilical cord blood, can be fixed with different types of fixing buffers, typically the commercial available ones, such as Cytocheck.

(2) The fixed human blood was tested on a hematology analyzer, like the XE-2100, to observe the scatter graphs, the nucleated red blood cell number and the nucleated red blood cell number per 100 white blood cells.

(3) The fixed blood is stored in different tubes or in ones tube with a large volume.

(4) The stored blood is tested on the hematology analyzer repeatedly, to observe the stability of nucleated red blood cell counting and staging.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure.

DETAILED DESCRIPTION OF THE PREFERRED EMBODIMENTS

Figure 1A:
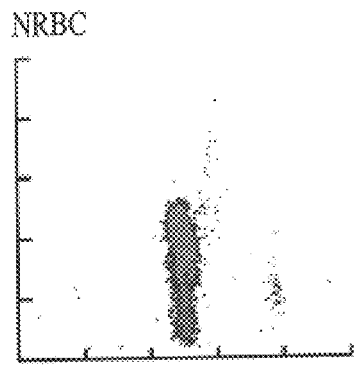
FIGS. 1a–1c are scatter graphs from different cell types tested by a hematology analyzer have revealed; Chicken red blood cells are only seen at top left (1a), white blood cells from SF-check are seen at top right (1b), and the mixture of the two are seen at bottom (1c)

In the present invention, the SF-check(control material) used in step (1) means that fixed human blood includes all the components of blood cells such as Red Blood Cells, White Blood Cells and Platelets. However, it is not limited to those blood components. Chicken red blood cells, with nuclei, are used for nucleated red blood cells. It can also include other types of animal red blood cells, with nuclei. Both of the cells can be pre-fixed and then mixed to make a mixture that can be used for the nucleated red blood cell counting and staging. The fixing buffers can be commercial or non-commercial reagents that can stabilize the cells that can be used for a longer period of time.

Different methods for quality control of nucleated red blood cells on a hematology analyzer were developed. One of them is a mixture of different fixed blood samples, which, carry different fluorescent intensities after the staining with a fluorescent dye on a hematology analyzer such as the XE-2100. The cell population can be divided, according to the XE-2100 nucleated red blood cell channel setting, into white blood cells and nucleated red blood cells in the nucleated red blood cell channel. This material showed stability for more than 50 days when it was stored at 40° C. The cell morphology showed good cell shape and the equipment showed stable nucleated red blood cell number and nucleated red blood cells per 100 white blood cells. Human blood cells were fixed with different fixing buffers. The fixed human peripheral blood and umbilical blood revealed good cell morphology in at least up to 50 days. During that time, the nucleated red blood cell number and nucleated red blood cells per 100 white blood cells showed very stable results. After then, the fixed blood still showed stable results in a narrow range within one standard deviation. When further studied, the fixed blood kept in separate tubes shows much more stable results than the blood that was repeatedly used over many times from one tube. The two methods were observed and showed good cell morphology and stability in long term storage at 4° C. These methods can be used for both quality control and calibrator material for nucleated red blood cell counting on a hematology analyzer like the XE-2100. The fixed blood may also be used for nucleated red blood cell staging.

In this invention, the fixed blood cells are from a human umbilical blood, peripheral blood with nucleated red blood cells, bone marrow, or any sample where white blood cells and nucleated red blood cells are present. The fixing buffer can be commercial or non-commercial which, makes the cells remain stable for a long period of time in order to monitor the nucleated red blood cell measurement on a given hematology analyzer, such as the XE-2100.

The mixture includes two cell populations. One is from animal blood, such as chicken red blood cells and the other is from a control material.(SF-check). The nucleated red blood cell number and the nucleated red blood cell number per 100 white blood cells can be obtained from this mixture. The chicken red blood cells were diluted in the control material(SF-check) in different concentrations and then tested on the hematology analyzer. This novel control material enables one to produce a measurement of cell populations for comparison purposes. This control number is then usable to diagnose or produce a prognosis for diseases. Table 1 shows the reproducibility of nucleated red in a control material(SF-check)-low and (SF-check)-high. Both of them showed very good reproducibility.

TABLE 1

Reproducibility of NRBC per one hundred WBC with mixture of NRBC in SF-low and SF-high. Both of them showed a CV of 3%.

| Number | SF-Low | SF-High |
|---|---|---|
| 1 | 269.70 | 17.10 |
| 2 | 256.00 | 16.70 |
| 3 | 260.40 | 18.00 |
| 4 | 260.20 | 18.00 |
| 5 | 268.10 | 17.30 |
| 6 | 261.70 | 18.00 |
| 7 | 251.80 | 18.20 |
| 8 | 247.20 | 17.60 |
| 9 | 246.20 | 18.10 |
| Count | 9.00 | 9.00 |
| Mean | 257.92 | 17.67 |
| SD | 8.38 | 0.52 |
| SE | 2.79 | 0.18 |
| Minimum | 246.20 | 16.70 |
| Maximum | 269.70 | 18.20 |
| Difference | 23.50 | 1.50 |
| CV | 0.03 | 0.03 |
| Median | 260.20 | 18.00 |

Figure 4:
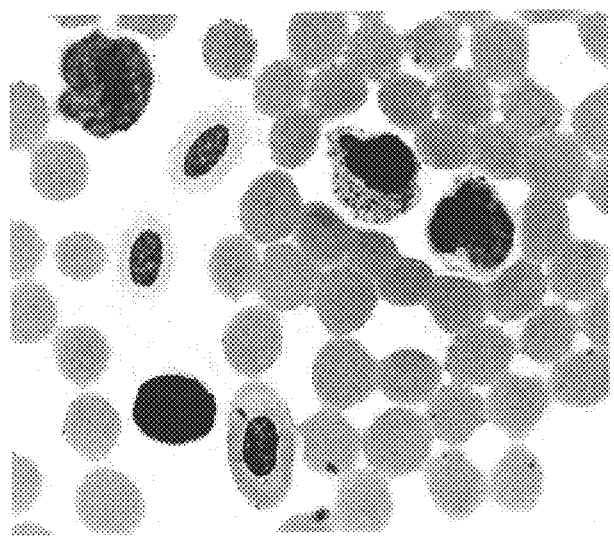
FIG. 4 illustrates cell morphology of chicken red blood cells in SF-check at 4° C. for 52 days.

FIG. 4 illustrates cell morphology of chicken red blood cells in SF-check(control material) at 4° C. being held for 52 days. The oval cells are chicken red blood cells. Other nucleic cells are white blood cells from SF-check(control material).

Figure 5:
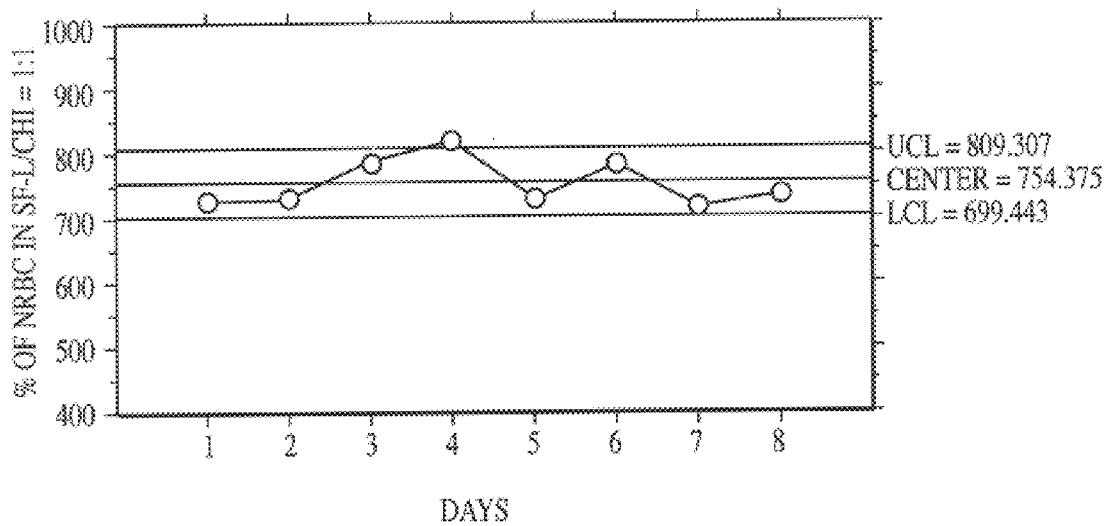
FIG. 5 graphically shows the stability of nucleated red blood cells/SF-check-low (1:1) in 52 days, when the blood mixture was kept at 4° C.
Figure 6A:
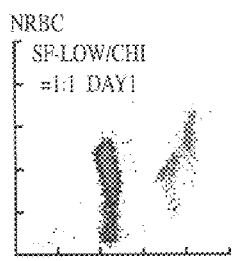
FIG. 6 illustrates scatter graphs of the chicken red blood cells in SF-check low kept for 52 days.
Figure 6B:
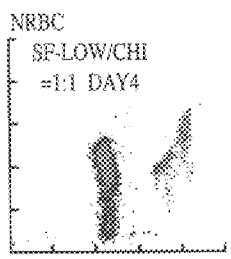
Figure 6C:
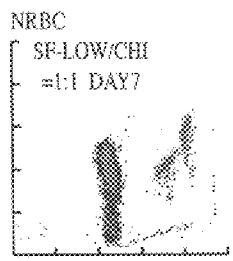
Figure 6D:
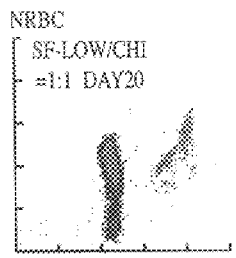
Figure 6E:
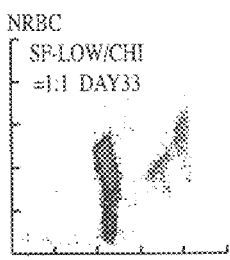
Figure 6F:
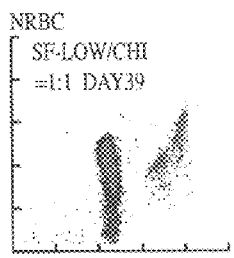
Figure 6G:
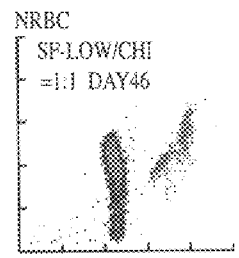
Figure 6H:
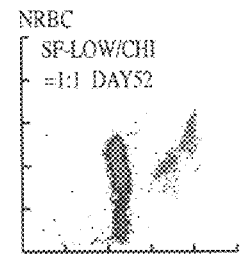

FIG. 5 graphically shows the stability of nucleated red blood cells/SF-check(control material)- in a 1:1 ratio in 52 days when the mixture was kept at 4° C.

FIG. 6 illustrates scatter graphs showing the chicken nucleated red blood cells in SF-check(control material) kept for 52 days. The scatter graphs from different days show no significant change.

Figure 7:
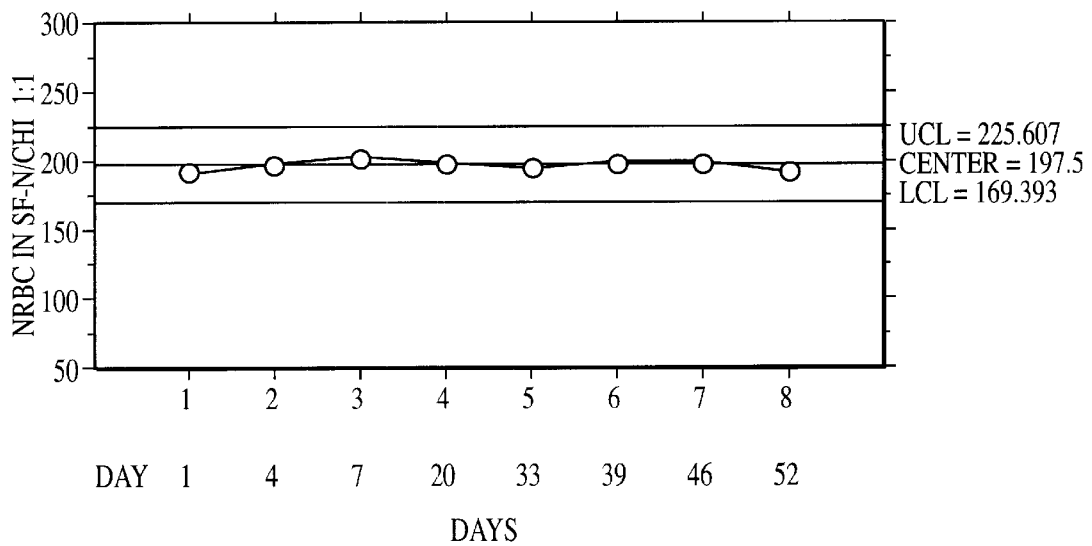
FIG. 7 graphically shows chicken red blood cells in SF-check-normal (1:1) kept for 52 days at 4° C.

FIG. 7 is a graphical representation of chicken nucleated red blood cells in SF-check(control material)-normal (1:1) kept for 52 days at 4° C.

Figure 8:
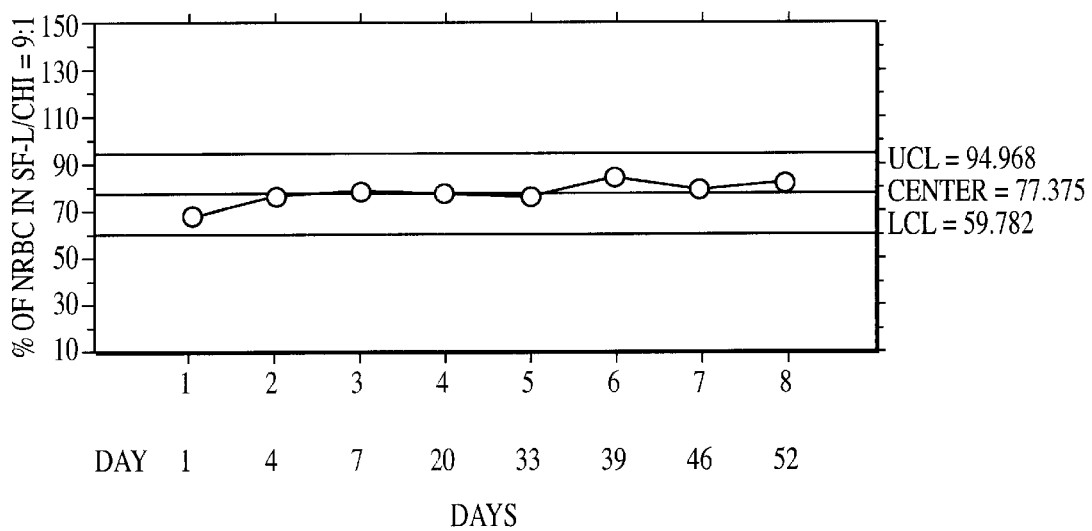
FIG. 8 graphically shows chicken red blood cells in SF-check-low (9:1) kept for 52 days at 4° C.

FIG. 8 depicts chicken red blood cells in SF-check-low (9:1) kept for 52 days at 4° C.

Figure 9:
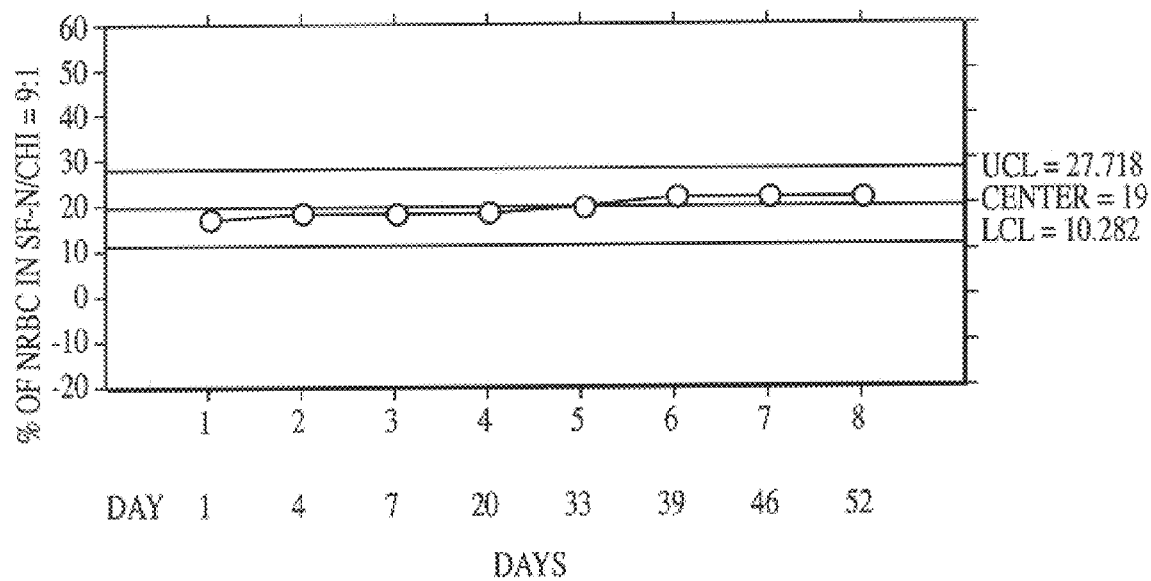
FIG. 9 graphically illustrates chicken red blood cells in SF-check-normal (9:1) kept for 52 days at 4° C.

FIG. 9 shows chicken red blood cells in SF-check-normal (9:1) kept for 52 days at 4° C.

Figure 10:
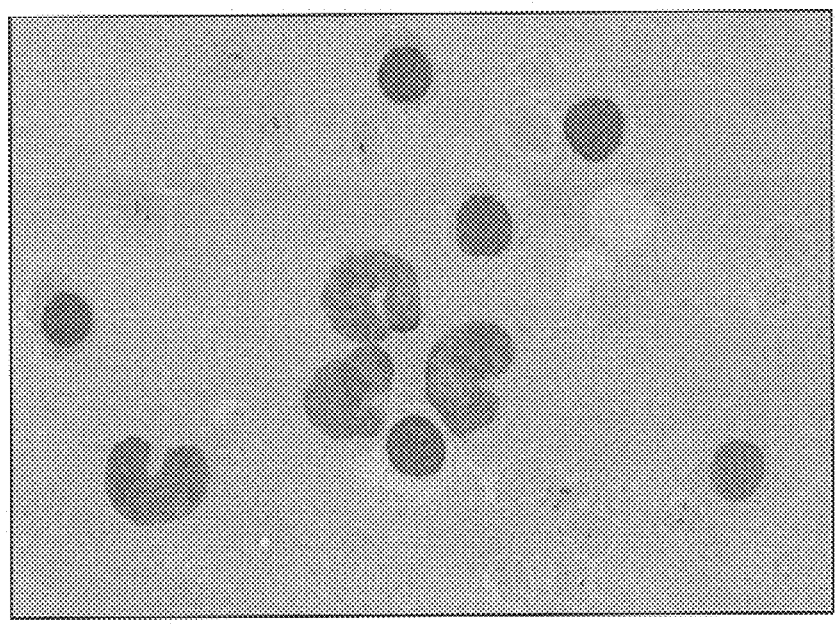
FIG. 10 illustrates human blood, fixed with a fixing buffer and kept for 52 days at 4° C.

FIG. 10 illustrates human blood fixed with a fixing buffer and kept for 52 days at 4° C.

Figures 11A, 11B, 11C, 11D:
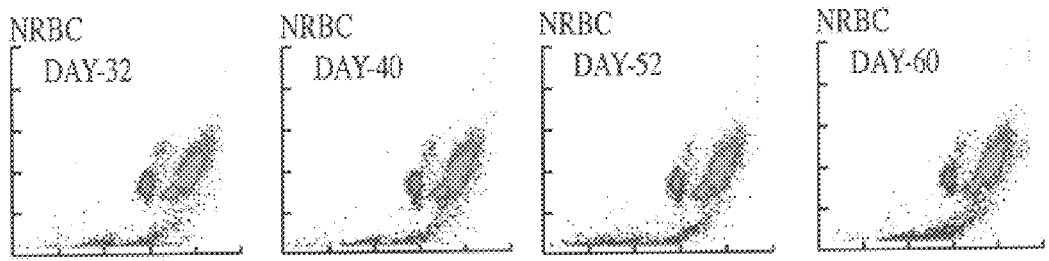
FIG. 11 shows fixed human blood stored for up to 60 days.

FIG. 11 shows fixed human blood stored for up to 60 days. The cell population in white blood cells and nucleated red blood cells show no change compared to day 1.

Figure 12:
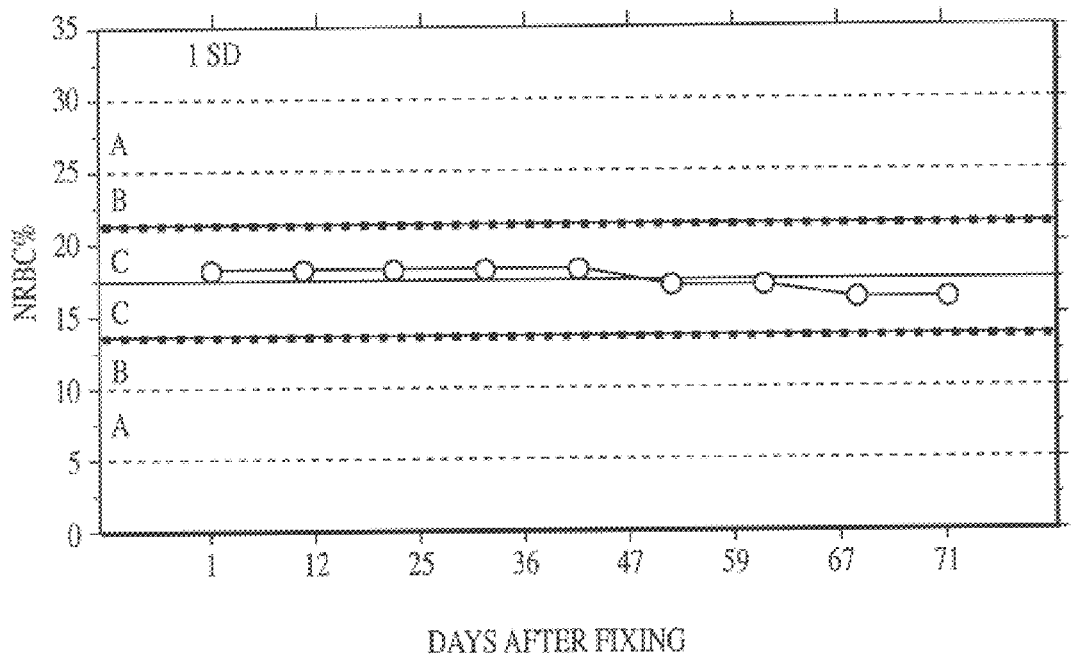
FIG. 12 graphically shows fixed blood stored for 71 days at 4° C.

FIG. 12 shows fixed blood stored for 71 days at 4° C. This illustrates very stable results for up to 63 days. After this time frame, the nucleated red blood cells decrease slightly, but they are still kept in the narrow range within one standard deviation.

TABLE 2

Test of fixed blood kept in individual tubes and used one tube each time or single tubes used repeatedly.

|  | Individual Tubes | Single Tube |
|---|---|---|
| Days Tested | 63 | 60 |
| Number | 7 | 7 |
| Average | 17.49 | 23.14 |
| Minimum | 16.6 | 16.4 |
| Maximum | 18 | 31.7 |
| Difference | 1.4 | 15.3 |
| CV % | 2.9 | 27.2 |
| SDD | 0.5 | 6.3 |

EXAMPLES

The method of quality control and calibration for nucleated red blood cell counting and staging of this present invention is described in further detail by way of examples.

Example 1

Quality control materials with different components were prepared:

(a) Mixture of SF-check(control material) prepared by Streck and chicken red blood cells by BioSure. This mixture provides cell numbers for white blood cells by SF-check and nucleated red blood cells by chicken red blood cell.

(b) Fixed human cord umbilical and peripheral bloods with nucleated red blood cells were used for nucleated red blood cell number and white blood cells. For this control material two different storage conditions were compared. One tube with sample was repeatedly tested and the other sample was divided into several tubes and tested only once per tube.

(c) The quality control materials were tested on the XE-2100 hematology analyzer and the nucleated red blood cell count was observed, on which, the X axis represents fluorescent intensity and the Y axis represents the cell size.

Figure 1B:
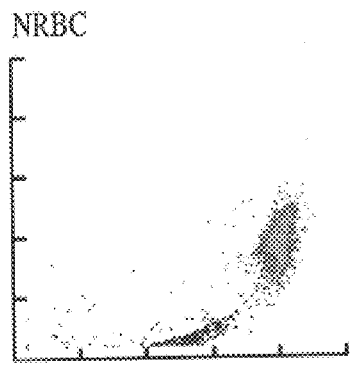
Figure 1C:
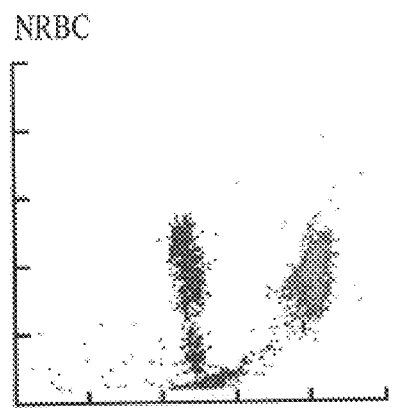
Figure 2A:
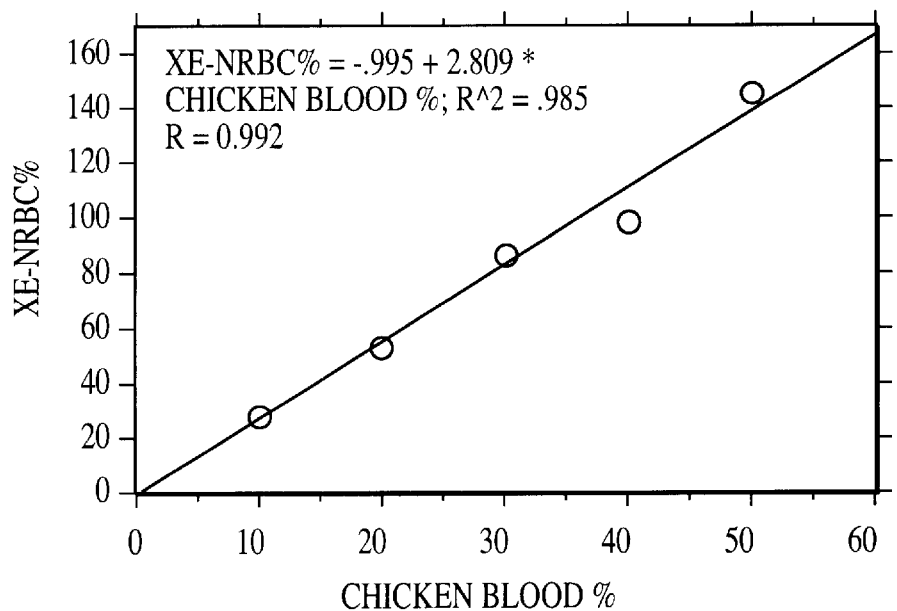
FIG. 2 graphically shows linearity of nucleated red blood cells in SF-check on a hematology analyzer.
Figure 2B:
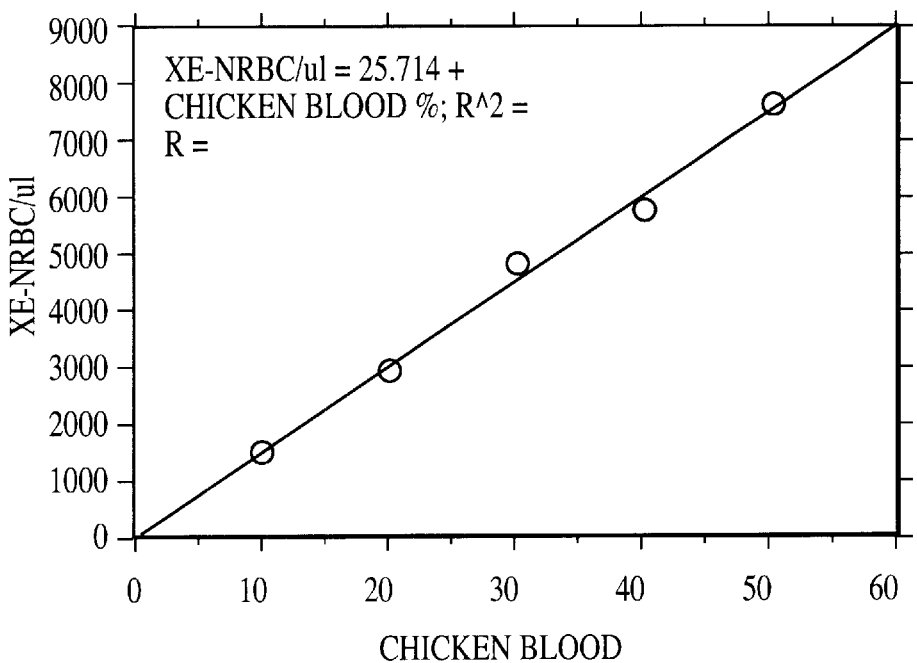
Figure 3:
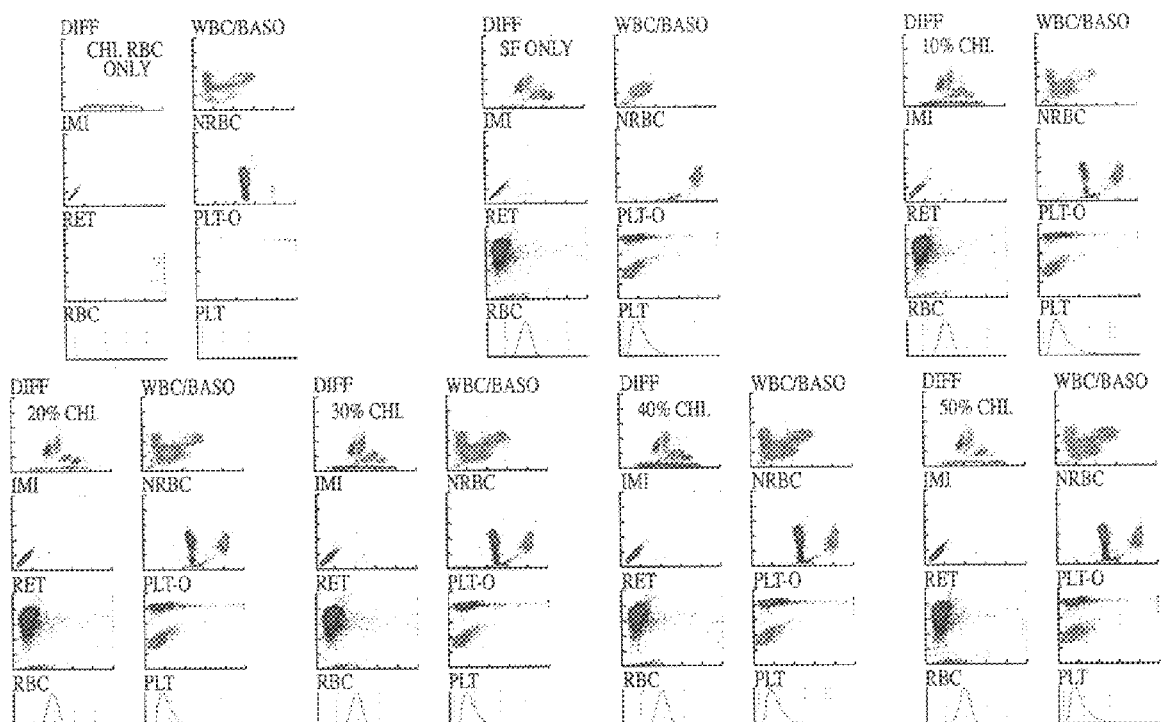
FIG. 3 illustrates graphs with different concentrations of nucleated red blood cells in a SF-check. There were nucleated red blood cells only (chicken red blood cells), SF-check only, and 10% to 50% of nucleated red blood cells in SF-check (v/v)

(d) FIG. 1 illustrates the cell populations from an SF-check and chicken red blood cells, before, and after mixing.

(e) FIG. 4 shows the cell morphology of the mixture of SF-check and chicken red blood cells at day 52, after mixing.

(f) FIG. 6 shows the nucleated red blood cell channel scatter graphs of the mixture at different time points. The graphs show no significant difference from storage at 4° C. for at least 50 days.

(g) The cell morphology of a fixed human peripheral blood stored for 52 days is shown in FIG. 10.

These examples reveal that the different samples of fixed blood used possess acceptable and stable cell morphology for both the nucleated red blood cell number and nucleated red blood cell count per 100 white blood cells.

The terms of degree such as substantially, about and approximately, as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing description of the embodiments according to the present invention are provided for illustration only, and not for the purpose of limiting the invention as defined by the appended claims and their equivalents.

What is claimed is:

1. A method for calibration and quality control of nucleated red blood cell counting on a hematology analyzer comprising providing a control material comprising a mixture of human and animal blood wherein the human blood is umbilical cord blood or peripheral blood containing nucleated red blood cells therein, and calibrating said nucleated red blood cell counting on said hematology analyzer by analyzing nucleated red blood cells in said control material with said analyzer.

2. The method as claimed in claim 1, wherein the control material provides measurable cell populations composed of white blood cells and nucleated red blood cells to facilitate counting of nucleated red blood cells and nucleated red blood cells per 100 white blood cells.

3. The method as claimed in claim 2, wherein the measurable cell populations are used as an indicator for diagnosis and prognosis of diseases.

4. The method as claimed in claim 2, wherein the measurable cell populations are controls for comparison with cell populations in bone marrow.

5. The method as claimed in claim 1, wherein the animal blood is chicken blood.

6. The method as claimed in claim 1, wherein the human blood further comprises a fixing buffer.

7. The method as claimed in claim 1, wherein cell size and fluorescent intensity is determined of the control material to facilitate a determination of nucleated red blood cell staging and biological change in the mixture.

\* \* \* \* \*